United States Patent [19]

Lawes

[11] Patent Number: 5,458,651
[45] Date of Patent: Oct. 17, 1995

[54] FEMORAL COMPONENT FOR A HIP PROSTHESIS

[75] Inventor: Peter Lawes, Maidenhead, England

[73] Assignee: Howmedica International, Shannon, Ireland

[21] Appl. No.: 9,162

[22] Filed: Jan. 26, 1993

[30] Foreign Application Priority Data

Jan. 28, 1992 [GB] United Kingdom .................... 9201734

[51] Int. Cl.⁶ .................................................. A61F 2/32
[52] U.S. Cl. .................................................. 623/23; 623/18
[58] Field of Search ........................... 623/16, 23, 18, 623/19, 20, 22

[56] References Cited

U.S. PATENT DOCUMENTS

| Re. 32,488 | 9/1987 | Gustilo et al. | 623/23 |
|---|---|---|---|
| 3,965,490 | 6/1976 | Murray et al. | 623/23 |
| 4,021,865 | 5/1977 | Charnley | 623/23 |
| 4,044,403 | 8/1977 | D'Errico | 623/23 |
| 4,359,785 | 11/1982 | Niederer | 623/23 |
| 4,430,761 | 2/1984 | Niederer et al. | 623/23 |
| 4,516,277 | 5/1985 | Butel | 623/23 |
| 4,693,724 | 9/1987 | Rhenter et al. | 623/23 |
| 4,714,470 | 12/1987 | Webb, Jr. et al. | 623/23 |
| 4,808,186 | 2/1989 | Smith | 623/23 |
| 4,921,501 | 5/1990 | Giacometti | 623/23 |
| 4,936,859 | 6/1990 | Morscher et al. | 623/23 |
| 4,938,770 | 7/1990 | Frey et al. | 623/23 |
| 4,944,759 | 7/1990 | Mallory et al. | 623/23 |
| 4,986,834 | 1/1991 | Smith et al. | 623/23 |
| 4,988,359 | 1/1991 | Frey et al. | 623/23 |
| 5,002,581 | 3/1991 | Paxson et al. | 623/23 |
| 5,007,931 | 4/1991 | Smith | 623/23 |
| 5,013,324 | 5/1991 | Zolman et al. | 623/23 |
| 5,047,062 | 9/1991 | Pappas et al. | 623/23 |
| 5,074,879 | 12/1991 | Pappas et al. | 623/23 |
| 5,080,680 | 1/1992 | Mikhail et al. | 623/23 |
| 5,133,766 | 7/1992 | Halpern | 623/23 |
| 5,152,799 | 10/1992 | Lyons | 623/23 |
| 5,171,324 | 12/1992 | Campana et al. | 623/23 |
| 5,197,989 | 3/1993 | Hinckfuss et al. | 623/23 |
| 5,197,990 | 3/1993 | Lawes et al. | 623/23 |

FOREIGN PATENT DOCUMENTS

| 0098224 | 1/1984 | European Pat. Off. | 623/23 |
|---|---|---|---|
| 0385585 | 9/1990 | European Pat. Off. | 623/23 |
| 0457464 | 11/1991 | European Pat. Off. | 623/23 |
| 2472374 | 7/1981 | France | 623/23 |
| 2528307 | 12/1983 | France | 623/23 |
| 2610823 | 8/1988 | France | 623/23 |
| 2639821 | 6/1990 | France | 623/23 |
| 1409054 | 10/1975 | United Kingdom | 623/23 |
| 2069340 | 8/1981 | United Kingdom | 623/23 |

OTHER PUBLICATIONS

Zimmer Catalog, Warsaw, Ind., Mar. 27, 1975.

Primary Examiner—David Isabella
Attorney, Agent, or Firm—Peter C. Richardson; Lawrence C. Akers; Raymond W. Augustin

[57] ABSTRACT

A femoral component of a replacement hip joint has a collarless stem including a shoulder for fixing in a medullary canal by cement. The component has a stem beneath the shoulder having a straight taper and the anterior and posterior faces of the stem each having a concave surface formed by a longitudinally extending curve from the top of the shoulder to the distal tip of the stem.

19 Claims, 4 Drawing Sheets

FEMORAL COMPONENT FOR A HIP PROSTHESIS

BACKGROUND OF THE INVENTION

1. Field of the Invention

This invention relates to a femoral component for use in a replacement hip joint.

2. Description of the Prior Art

The Exeter type femoral component of the kind shown in British Patent Specification No. 1 409 054 is well known and comprises a neck which carries a ball head for cooperation with an acetabular socket. The neck is connected to a collarless stem which includes a shoulder, the stem beneath the shoulder having a straight taper. Thus there is no collar for resting either on the bone or the cement in the area where the stem joins the neck of the implant. This type of stem has evolved so that the stem can be given a polished finish to help it slide down inside the bone cement. The term "straight taper" in relation to the stem refers to the center line axis of the shape of the stem. The present invention relates to this type of femoral component. A tapered hip having a flange to enhance load transfer is shown in U.S. Pat. No. 4,021,865 dated May 10, 1977.

SUMMARY OF THE INVENTION

According to the present invention a femoral component of a replacement hip joint has a collarless stem including a shoulder, for fixing in a medullary canal by cement, the stem beneath the shoulder having a straight taper and the anterior and posterior faces of the stem having a concave surface formed by a longitudinally extending curve from the top of the shoulder to the distal tip of the stem.

Preferably the lateral and medial surfaces of said stem beneath said shoulder also each have a concave surface formed by a longitudinally extending curve.

Thus the concavity of each of the faces only exists in one plane for each face, for example, that for the anterior face can only be seen when viewed from the direction of the lateral or medial face.

The effect of the concave surfaces is that the taper angle is slightly steeper than in the known constructions, on the proximal part of the stem, that is the end near the hip joint bearing surface, and shallower at the tip or distal end.

At the hip joint bearing surfaces all the load transfers from the acetabular component into the femoral component of the implant. Beyond the distal end of the femoral component stem all this load has been transferred into the bone. Between the cut end of the femur proximally and the distal tip of the femoral stem the load gradually transfers from the implant into bone. The distribution of this load transfer along the length of the femoral stem is influenced at each cross-sectional level by the relative stiffness of the implant, the bone cement mantle and the surrounding bone. Many femoral hip stem implants have large cross-sections near their distal tip giving high sectional stiffness and this causes a high proportion of the load from the bearing surface to be retained within the implant and transferred out through the bone cement mantle into the bone near the distal end of the implant. Conversely, stems which are very flexible distally (by virtue of the choice of material modulus or sectional geometry) cause a greater proportion of the load to be transferred into the bone at or near the proximal end of the femur. In the extreme the absolutely flexible stem has a stiffness of zero, that is the distal stem has been designed out, and all the load transfer occurs through whatever proximal portion of the stem has been left by the designer.

The arrangement according to the invention therefore provides relative rigidity at the top end of the implant which is greater than the distal end. This transfers more load from the hip stem onto the bone through the bone cement mantle at the top and less passes down the stem and is transferred out into the bone at the distal end. Transfer of load onto the top end of the femur is thought to be beneficial in order to avoid bone resorption.

A further advantage is that at the present in some patients a point about half way up the stem in existing devices is found to come very close to the internal bone wall and leaves very little space for cement. Thus although the existing type of stem has straight tapering edges the inside form of the cortical bone is more trumpet shaped. Therefore, by providing concave surfaces on the stem the thickness of the cement mantle thickness laterally in this area can be increased to a more acceptable thickness, at least 1 mm and preferably 1 ½ mm–2 mm.

It is important in the present arrangement that the edges and side faces of the stem never become parallel because this will lose the advantage of taper locking engagement either before or after any subsidence. The stem must be always narrowing as it progresses downwards but it is not necessary to maintain a constant taper angle.

The stem can have a rectangular, elliptical or trapezoidal cross-section, and at the distal tip it can be substantially circular.

Preferably the surface of the stem is polished and it can be used with a distal void centralizer.

It has been found to be advantageous to avoid the use of any grooves, notches, holes, ridges, matt surfaces, macro surfaces as these tend to impair the engagement efficiency of the stem.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views.

DESCRIPTION OF THE PREFERRED EMBODIMENT

Figure 1:
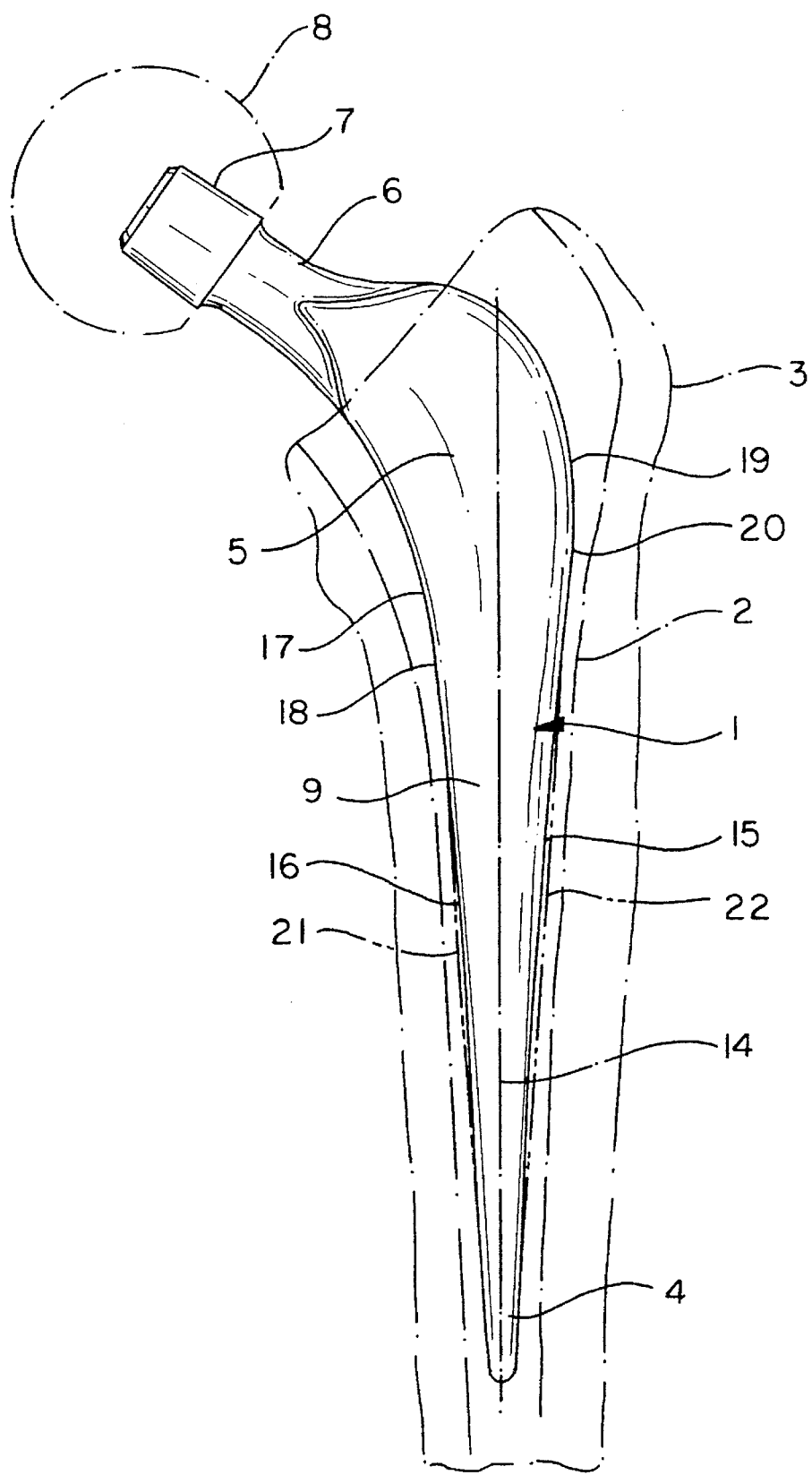
FIG. 1 is a side elevation of a femoral component according to the present invention.

As shown in the drawings the femoral component of a replacement hip joint has a straight collarless stem 1 of substantially rectangular cross-section. The stem is intended for fixing in position in a medullary canal 2 of a femur indicated by broken lines 3 by cement in well known manner. The stem has a continuous taper from its distal end 4 to a shoulder 5 where it merges into a neck 6. The neck 6 communicates with a boss 7 to receive a ball head indicated by broken lines 8 which will cooperate with an acetabular socket.

As will be seen from the drawings the anterior side face 9 of the stem including the collar 5 is substantially flat until it merges into the neck 6 which is of circular cross-section. The posterior side face 10 is of similar configuration. These faces are radiused with a longitudinally extending curve so that they are concave. The radii are all located on planes parallel to a plane extending from the anterior side to the posterior side through center line 14 of stem 1 (A-P plane). Broken lines 12 and 13 indicated the straight line shape if there was no concavity. This shape extends from the distal tip 4 and up through the shoulder 5 on these faces to the neck 6. At the upper end there is a high concave radius as indicated by reference numeral 11, the radius decreasing thereafter and finally running out at the distal tip 4.

The center line of the tapering straight lower stem portion is indicated at 14.

The lateral face 15 and medial face 16 of the stem are also tapered below the shoulder 5. The curving inner medial face 17 of the shoulder 5 merges into the straight tapering portion of the stem at a point 18 and the convex surface 19 on the lateral face of the shoulder 5 merges into the straight tapering stem at the point indicated by reference numeral 20.

Below the points 18 and 20 the surfaces of lateral and medial faces 15 and 16 are shaped concave. The relative straight line shapes of the faces if they were not concave are shown by broken lines 21, 22.

A relatively large radius is employed on these lateral and medial faces. The radii are all located on planes parallel to a plane extending from the lateral to the medial sides through centerline 14 of stem 1 (M-L plane). The maximum depth of concavity away from the straight surface from which they are cut is about 1 mm-2 mm.

For a stem length of typically 150 mm (the implanted or cemented section) the position of maximum depth of concavity would be typically one-half to two-thirds down the length of the stem portion on the lateral side. On the medial side the entire geometry from tip to neck becomes a complex radius.

Figure 3:
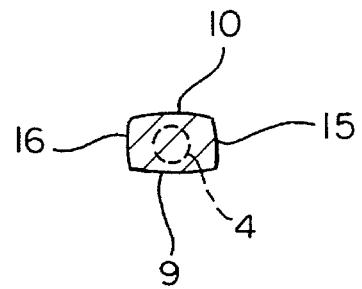
FIG. 3 is a cross-sectional plan view on line III—III of FIG. 2.

The cross-section of the stem as shown in FIG. 3 is substantially rectangular with radiused corners, The surfaces can be flat but in the arrangement shown they are slightly bowed outwardly. At the distal tip 4 the rectangular cross-section becomes substantially circular.

In the arrangement shown the femoral component is intended for use with a removable ball head 8 but if desired the ball head could be integral with the stem.

The surface of the stem, incorporating the shoulder, is highly polished and if desired a distal void centralizer, for example of the kind set forth in U.S. Pat. No. 5,092,892 can be used with it.

Figure 2:
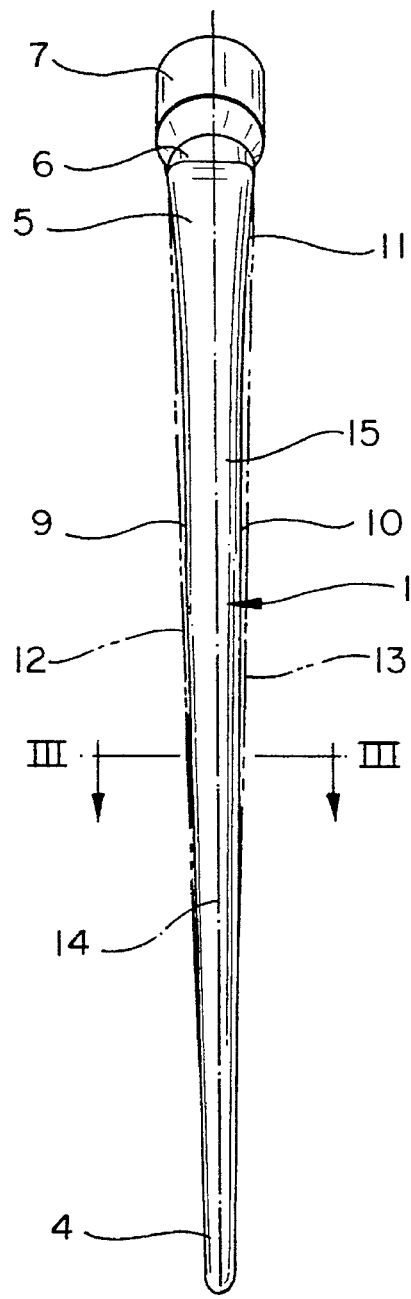
FIG. 2 is an end elevation of the component shown in FIG. 1.
Figure 4:
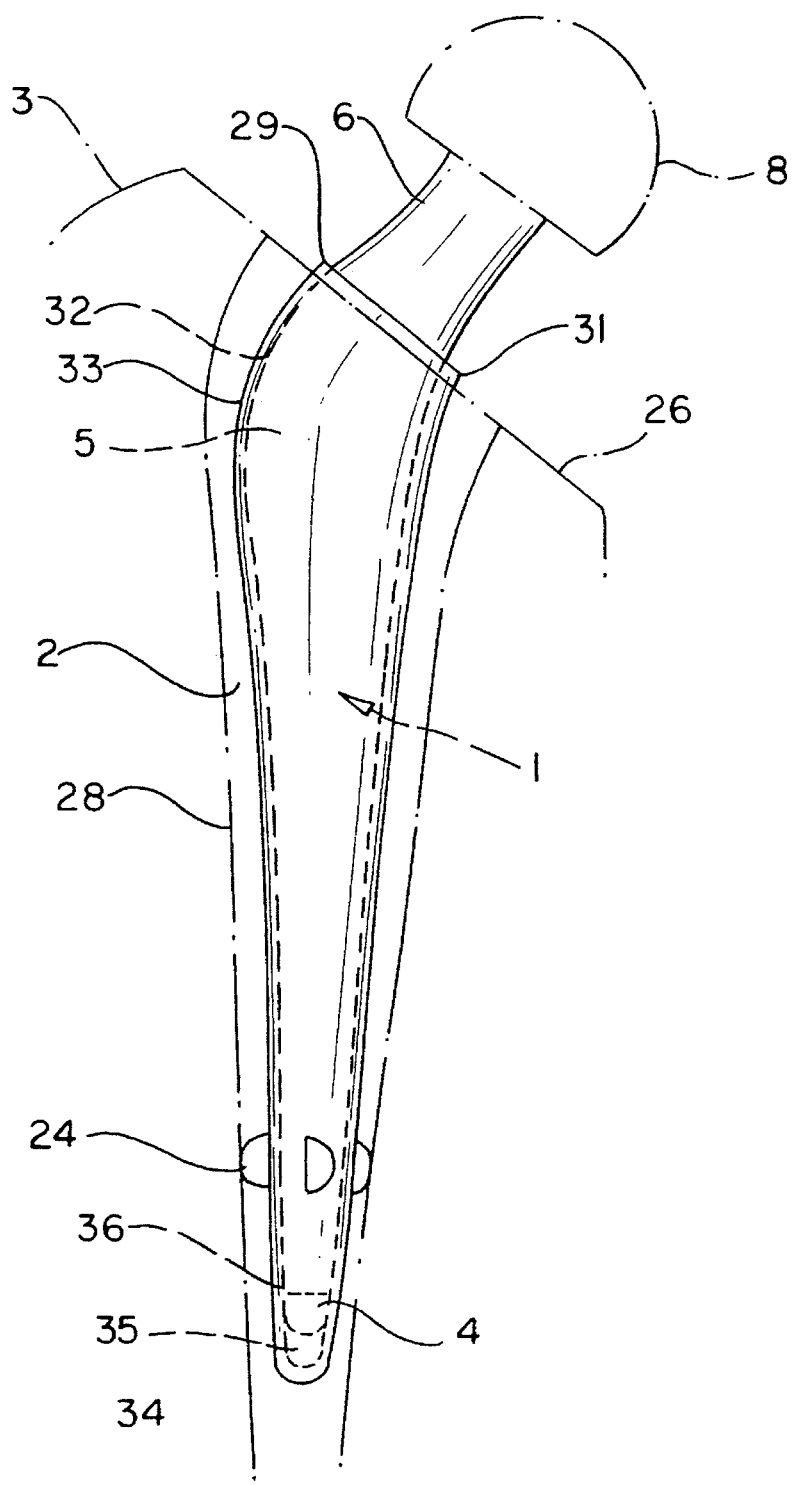
FIG. 4 is a side elevation of a femoral component incorporating a sheath as set out in British Patent Application No. 9011132.6 (U.S. application Ser. No. 07/701,556)
Figure 5:
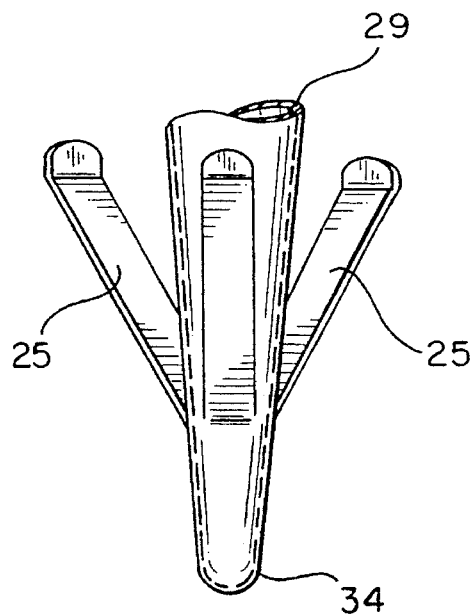
FIG. 5 shows the distal end of a sheath as shown in FIG. 4 but of a different configuration.

FIGS. 4 and 5 show how a sheath can be included and the same reference numerals are used to indicate similar parts to FIGS. 1, 2 and 3.

As shown in FIG. 4 the stem 1 is enclosed in a sheath 29 which covers the stem from its distal tip 4 to a location adjacent the proximal cut end 2 of the femur 3. In the arrangement shown this end 31 of the sheath is shown slightly protruding from the cement mantle 28 and has a cut-out opening 32 extending from its end 31 to a point 33, to assist assembly.

The sheath is made from a material similar to bone cement material, for example polymethylmethacrylate, and its distal end 34 is somewhat longer than the end 4 of the stem 1 to create a void 35. The internal side walls of the distal end 34 can be parallel up to a point about 1–2 cm from the end 4 of the stem as indicated by reference numeral 36.

The thickness of the sheath is about 1 mm and can be made as a separate molding.

Optionally molded into the sheath are four thin outwardly projecting abutments 24 in the form of four equally spaced tangentially projecting wings or arms. These abutments act as a centralizer and to hold the stem 1 away from the wall of the medullary canal during implantation.

The projections can resiliently deform circumferentially inwardly as the stem, together with the sheath, is pushed into place in the canal 2.

With the sheath in position the centralizer provided by the abutments becomes well integrated with the cement, as does the remains of the sheath thus avoiding any weakening or hole creation.

If there is now a tendency for the stem to move further into the cement mantle this is accommodated by movement within the sheath which, it will be appreciated, has become integral with the cement mantle itself but, because it is not connected to the stem adhesion between the cement and the stem is reduced and therefore the frictional resistance to the subsiding action or re-engagement of the stem is reduced.

An alternative construction of the sheath is shown in FIG. 5 and in which similar reference numerals are used to indicate similar parts.

With this arrangement the void 35 is again created when the sheath 29 is placed on the stem 1 (not shown in FIG. 5). In this construction however the abutments 24 are provided by three radially and upwardly extending arms 25 spaced around the sheath and which again act to centralize the stem in the medullary canal.

Figure 6:
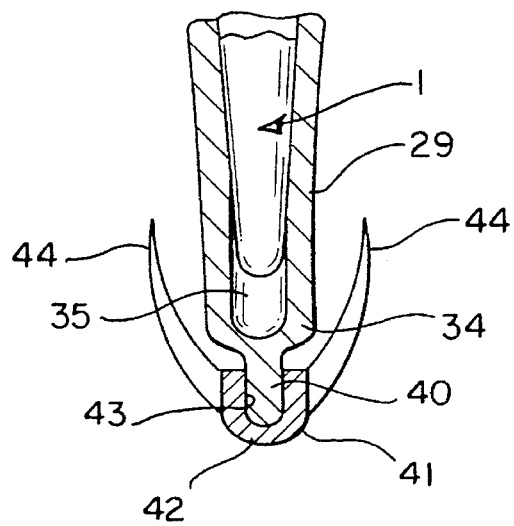
FIG. 6 is a cross-sectional elevation of the distal end of an alternative construction employing a separate centralizer.

In an alternative and preferred construction a separate centralizer is used as shown in FIG. 6. In this construction the same reference numerals are used to indicate similar parts to those shown in FIGS. 4 and 5, but no centralizer abutments 24 are provided on the sheath itself. The distal end 34 of the sheath has a spigot 40 on which is located a separate centralizer 41 which comprises a central boss 42 having a blind bore 43 which is a push fit onto the spigot 40. Three radially and upwardly projecting arms 44 extend outwardly from the central boss 42 and act to centralize and hold the stem 1 away from the wall of the medullary canal in a similar manner to the abutments 24. The centralizer 41 can be made from the same material as the sheath but filler can be added to improve the flexibility of the projecting arms 44.

When the prosthesis is to be implanted the surgeon fits the appropriate size of preformed sheath to the stem of the prosthesis, the sheath including the integrally formed centralizer with a void creator on the distal tip. The assembled stem and sheath are then inserted into the bone cavity which has already been filled with normal bone cement in the normal way. The preformed cement sheath bonds directly with the bone cement inserted by the surgeon. The material of the sheath and the cement are identical or compatible so that they are bonded together.

It is important that the preformed sheath is separate from the stem, it cannot be provided merely by a coating applied to the stem as this will not give the same low friction characteristics at the surface of the stem which are required.

It is possible to provide a lubricant between the preformed sheath and the stem in order to reduce friction still further, a suitable sterile lubricant being used, for example sterile liquid paraffin.

This kind of construction is intended to provide an optimization of the interface conditions between the cement in an intramedullary canal and the surface of the stem. The avoidance of windows in the cement and direct contact between metal and bone is also an advantage.

While several examples of the present invention have been described, it is obvious that many changes and modifications may be made thereunto, without departing from the spirit and scope of the invention.

I claim:

1. A femoral component of a replacement hip joint for implanting into the medullary canal of a femur having a proximal cut end comprising:

a smooth collarless stem having a generally rectangular cross-section with an anterior face, a posterior face, a distal tip and including a shoulder for fixing in a medullary canal by cement, said stem distally of the shoulder having a taper with respect to a longitudinal axis of said stem and the anterior and posterior faces of said stem each having a concave surface extending continuously across said faces formed by a longitudinally extending curved surface from said shoulder continuously to the distal tip of said stem, said concave surface having a maximum depth of 2 mm compared to a tapered planar surface extending from said shoulder to said distal tip along said anterior and posterior faces, radii forming said longitudinal curved surface to each point on the curved surface lying in a plane parallel to an anterior-posterior plane through said longitudinal axis.

2. The femoral component of a replacement hip joint as claimed in claim 1 further including a lateral and a medial face, wherein the lateral and medial faces of said stem distally of said shoulder also each have a concave surface extending continuously across said faces formed by a continuous longitudinally extending curved surface, radii forming said longitudinal curve to each point on the curved surface lying in a plane parallel to a medial-lateral plane through said longitudinal axis.

3. The femoral component of a replacement hip joint as claimed in claim 1 wherein the stem has a rectangular, elliptical or trapezoidal cross-section.

4. The femoral component of a replacement hip joint as claimed in claim 1 wherein the stem has a substantially circular cross-section at the distal tip.

5. The femoral component of a replacement hip joint as claimed in claim 1 wherein the stem is polished.

6. The femoral component of a replacement hip joint as claimed in claim 1 wherein the stem is provided with means to receive a ball head.

7. The femoral component of a replacement hip joint as claimed in claim 1 wherein the stem is provided with a modular ball head.

8. The femoral component of a replacement hip joint as claimed in claim 1 wherein stem is provided with a sheath made from an acrylic material.

9. The femoral component of a replacement hip joint as claimed in claim 8 wherein said sheath is dimensioned to enclose the stem from the distal tip to a location on the stem which will be adjacent the proximal cut end of the femur with which it will be used.

10. The femoral component of a replacement hip joint as claimed in claim 8 wherein the sheath is dimensioned and constructed to allow the stem to move further into it under load.

11. The femoral component of a replacement hip joint as claimed in claim 8 wherein the sheath has a distal end in the form of a cup, an inner end surface of which is spaced away from the distal tip of the stem to provide a void.

12. The femoral component of a replacement hip joint as claimed in claim 11 wherein said sheath has means for centralizing the stem in the medullary canal of the femur with which it is to be used.

13. The femoral component of a replacement hip joint as claimed in claim 12 wherein the centralizing means includes outwardly projecting resiliently deformable abutments.

14. The femoral component of a replacement hip joint as claimed in claim 12 further including a centralizer which is adapted to fit on the distal end of the sheath.

15. A collarless femoral component for a replacement hip having anterior, posterior, lateral and medial faces, said component comprising:

a proximal head region; and a distal stem region, said stem region having a polished outer surface and having a cross-section symmetrical about a straight longitudinally extending axis, the medial, lateral, posterior and anterior faces of said stem region each having a continuous concave surface formed by a longitudinal curve extending along said distal stem region from a distal tip thereof to the head region, said concave surface having a maximum depth of 2 mm compared to a tapered planar surface extending from said shoulder to said distal tip along said anterior and posterior faces, a radius from a center of said longitudinal curve along said anterior and posterior faces to each point on the curve lies in a plane parallel to an anterior-posterior plane through said longitudinal axis, a radius from a center of said longitudinal curve along said medial and lateral faces to each point on the curve lies in a plane parallel to a medial-lateral plane through said longitudinal axis.

16. A femoral component of a replacement hip joint for implantation into the medullary canal of a femur having a proximal cut end comprising:

a smooth collarless stem having a generally rectangular cross-section with an anterior face, a posterior face, a distal tip and including a shoulder for fixing in a medullary canal by cement, said stem distally of the shoulder having a straight taper and the anterior and posterior faces of said stem each having a continuous concave surface formed by a longitudinal curve extending continuously from said shoulder to the distal tip of said stem, said concave surface having a maximum depth of 2 mm compared to a tapered planar surface extending from said shoulder to said distal tip along said anterior and posterior faces, wherein said stem is provided with a sheath made from an acrylic material.

17. The femoral component of a replacement hip joint as claimed in claim 16 wherein the sheath has a distal end in the form of a cup, an inner end surface of which is spaced away from the distal tip of the stem to provide a void.

18. The femoral component of a replacement hip joint as claimed in claim 16 wherein said sheath has means for centralizing the stem in the medullary canal of the femur with which it is to be used.

19. The femoral component of a replacement hip joint as claimed in claim 18 wherein the centralizing means includes outwardly projecting resiliently deformable abutments.

* * * * *